(12) United States Patent
Barney et al.

(10) Patent No.: US 7,503,324 B2
(45) Date of Patent: Mar. 17, 2009

(54) PRE-METERED DOSE MAGAZINE FOR DRY POWDER INHALER

(75) Inventors: Brian Barney, Great Dunmow (GB); David O'Leary, Little Thurrock Grays (GB); Esther Perea-Borobio, London (GB); Andrew Dickson, Harlow (GB); Sophia Chew, London (GB); Rachel Striebig, London (GB)

(73) Assignee: Norton Healthcare Ltd (GB)

( * ) Notice: Subject to any disclaimer, the term of this patent is extended or adjusted under 35 U.S.C. 154(b) by 510 days.

(21) Appl. No.: 10/783,796

(22) Filed: Feb. 20, 2004

(65) Prior Publication Data

US 2006/0157053 A1    Jul. 20, 2006

(30) Foreign Application Priority Data

Feb. 20, 2003    (GB) ................... 0303870.0

(51) Int. Cl.
*A61M 15/00*    (2006.01)
*A61M 16/00*    (2006.01)
(52) U.S. Cl. ................. 128/203.21; 128/203.15
(58) Field of Classification Search ........... 128/200.11, 128/200.12, 200.14, 200.17, 200.24, 203.12, 128/203.15, 203.19, 203.21, 203.22, 203.23
See application file for complete search history.

(56) References Cited

U.S. PATENT DOCUMENTS

| 5,441,060 | A | * | 8/1995 | Rose et al. ............... 131/271 |
| 5,503,144 | A | | 4/1996 | Bacon et al. |
| 6,665,381 | B1 | | 12/2003 | Nassimi |
| 6,748,947 | B2 | * | 6/2004 | Keane et al. ............ 128/203.15 |
| 6,880,555 | B1 | * | 4/2005 | Brunnberg et al. ..... 128/203.12 |
| 7,093,595 | B2 | * | 8/2006 | Nesbitt .................. 128/203.15 |
| 7,171,965 | B2 | * | 2/2007 | Young et al. ........... 128/203.15 |

\* cited by examiner

*Primary Examiner*—Justine R Yu
*Assistant Examiner*—Annette F Dixon
(74) *Attorney, Agent, or Firm*—Lerner, David, Littenberg, Krumholz & Mentlik, LLP

(57) ABSTRACT

A dry powder inhaler including a housing having a mouthpiece and a delivery passageway connected to the mouthpiece, a magazine positioned within the housing and including a plurality of reservoirs for holding doses of dry powder, and wherein the magazine is movable within the housing so that the reservoirs are sequentially positioned within the delivery passageway of the housing upon movement of the magazine, a cover connected to the housing and movable to open and close the mouthpiece of the housing, and a rake connected to the cover, extending into the housing and engageable with the magazine so that, upon the cover being moved to open the mouthpiece, the rake moves the magazine and causes one of the reservoirs of the magazine to be positioned within the delivery passageway.

13 Claims, 15 Drawing Sheets

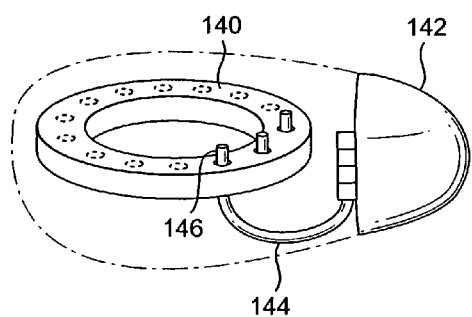 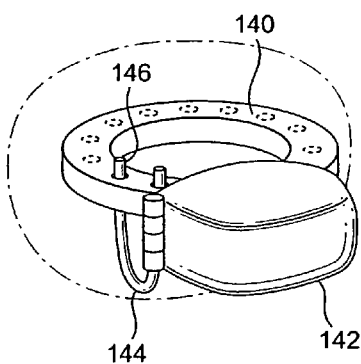
FIG. 24　　　　　　　FIG. 25
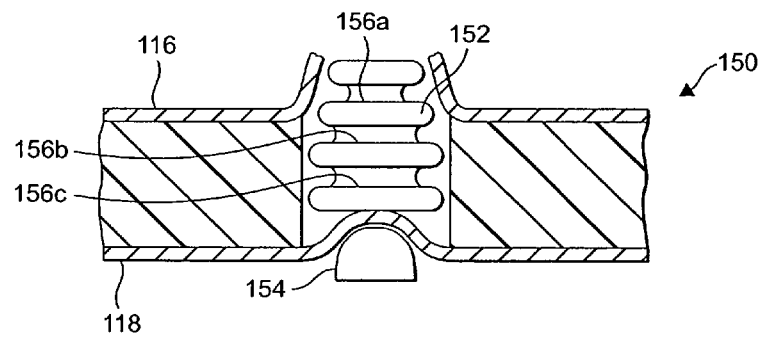
FIG. 26
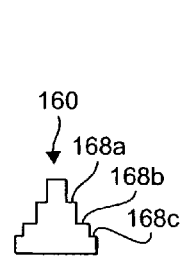 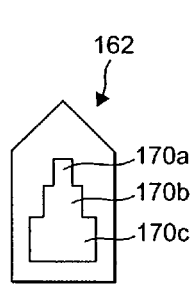 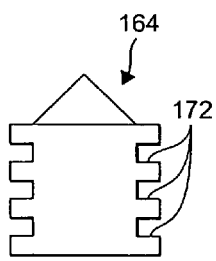 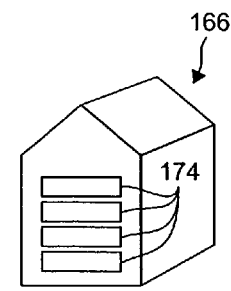
FIG. 27　　FIG. 28　　FIG. 29　　FIG. 30

PRE-METERED DOSE MAGAZINE FOR DRY POWDER INHALER

CROSS-REFERENCE TO RELATED APPLICATIONS

The present application claims priority of United Kingdom Patent Application No. 0303870.0, filed on Feb. 20, 2003.

FIELD OF THE DISCLOSURE

The present disclosure relates to a dry powder inhaler for administering dry powder medicament to a patient. More particularly, the present disclosure relates to a magazine having a plurality of individually separated, pre-metered doses for a breath-actuated dry powder inhaler and a method for providing pre-metered doses of dry powder medicament for inhalation by a patient.

BACKGROUND OF THE DISCLOSURE

Metered dose medicament inhalers are well known for dispensing medicament to the lungs of a patient. In most cases, the inhalers include a reservoir containing dry powder medicament in bulk form, and means for metering the medicament from the reservoir in discrete amounts for inhalation by a patient.

For example, U.S. Pat. No. 5,503,144, which is assigned to the assignee of the present disclosure shows a breath-actuated dry-powder inhaler having a medicament reservoir. The reservoir contains dry powder medicament in bulk form, and the inhaler includes a metering chamber for removal of the powdered medicament from the reservoir in discrete amounts. The inhaler also includes an air inlet for entraining the removed powdered medicament through a mouthpiece upon patient inhalation. The reservoir and metering chamber of the inhaler shown by U.S. Pat. No. 5,503,144 properly function to dispense discrete amounts of powdered medicament to a patient.

U.S. Pat. No. 6,655,381, which is assigned to the assignee of the present disclosure shows a pre-metered dose assembly for consistently supplying precise doses of medicament for a dry powder inhaler. The assembly includes a cap defining a dry powder delivery passageway and a magazine including a plurality of separate reservoirs for holding pre-metered doses of dry powder. The cap is movable with respect to the magazine for sequentially positioning the reservoirs within the delivery passageway of the cap. A breath-induced low pressure through the dry powder delivery passageway of the assembly entrains dry powder from the reservoir positioned in the passageway for inhalation by a patient using the inhaler. Providing the powdered medicament in pre-metered doses further ensures that the medicament is consistently dispensed to a patient in precise doses.

What is still desired is a new and improved dry powder inhaler for administering dry powder medicament to a patient. The dry powder inhaler will also preferably include a magazine having a plurality of individually separated and sealed, pre-metered doses and mechanisms for advancing the magazine during use and for deploying the doses from the magazine for inhalation by a patient using the inhaler.

SUMMARY OF THE DISCLOSURE

The present disclosure provides a dry powder inhaler including a housing having a mouthpiece and a delivery passageway connected to the mouthpiece, a magazine positioned within the housing and including a plurality of reservoirs for holding doses of dry powder, and wherein the magazine is movable within the housing so that the reservoirs are sequentially positioned within the delivery passageway of the housing upon movement of the magazine, a cover connected to the housing and movable to open and close the mouthpiece of the housing, and a rake connected to the cover, extending into the housing and engageable with the magazine so that, upon the cover being moved to open the mouthpiece, the rake moves the magazine and causes one of the reservoirs of the magazine to be positioned within the delivery passageway.

Further features and advantages of the presently disclosed pre-metered dose magazine and method for providing pre-metered doses will become more readily apparent to those having ordinary skill in the art to which the present disclosure relates from the following detailed description and attached drawings.

BRIEF DESCRIPTION OF THE DRAWINGS

So that those having ordinary skill in the art will more readily understand how to construct a pre-metered dose magazine and dry powder inhaler in accordance with the present disclosure, exemplary embodiments are described in detail below with reference to the drawing figures wherein:

FIG. 1 is a side and top isometric view of an exemplary embodiment of a dry powder inhaler according to the present disclosure including a housing having a mouthpiece cover shown in a closed position;

FIG. 2 is a front and top isometric view of the inhaler of FIG. 1, with the mouthpiece cover shown in an opened position to expose a mouthpiece of the inhaler;

FIG. 3 is a bottom plan view of a upper portion of the housing of the inhaler of FIG. 1;

FIG. 4 is a top plan view of a lower portion of the housing of the inhaler of FIG. 1;

FIG. 5 is a top plan view of a dose magazine of the inhaler of FIG. 1;

FIG. 6 is a side elevation view of the dose magazine of the inhaler of FIG. 1;

FIG. 7 is a top plan view of a cup-like base of a de-agglomerator of the inhaler of FIG. 1;

FIG. 8 is a bottom isometric view of a top piece of the de-agglomerator of the inhaler of FIG. 1;

FIG. 9 is a side elevation view of the cup-like base of the de-agglomerator of the inhaler of FIG. 1;

FIG. 10 is a top plan view of the mouthpiece cover of the inhaler of FIG. 1, showing a magazine advancement rake pivotally extending from the cover;

FIG. 11 is a side elevation view of the mouthpiece cover and advancement rake of the inhaler of FIG. 1;

FIG. 12 is a top plan view of an exemplary embodiment of a dose magazine constructed in accordance with the present disclosure;

FIG. 13 is a sectional view of the dose magazine taken along line 13-13 of FIG. 12;

FIG. 14 is a top plan view of the dose magazine of FIG. 12, shown with an upper foil layer removed;

FIG. 15 is a top plan view of another exemplary embodiment of a dose magazine constructed in accordance with the present disclosure;

FIG. 16 is a sectional view of the dose magazine taken along line 16-16 of FIG. 15;

FIG. 17 is a top plan view of an additional exemplary embodiment of a dose magazine constructed in accordance with the present disclosure;

FIG. 24 is a side perspective view of additional exemplary embodiments of a dose magazine, a mouthpiece cover and an actuator, all constructed in accordance with the present disclosure, and wherein the actuator is adapted to cause a medicament piston to be deployed from the magazine upon the mouthpiece cover being opened;

FIG. 25 is a front perspective view of the dose magazine, the mouthpiece cover and the actuator of FIG. 24;

FIG. 26 is a sectional view of a further exemplary embodiment of a dose magazine, a medicament piston, and an actuator shown deploying the piston, all constructed in accordance with the present disclosure;

FIGS. 27 through 30 are side views of various exemplary embodiments of medicament pistons constructed in accordance with the present disclosure;

Figure 57:
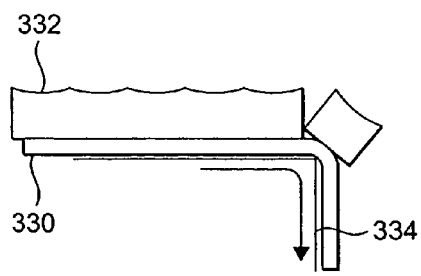
Figure 58:
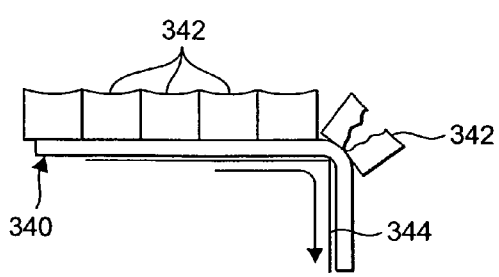

FIG. 57 is a side elevation view of an exemplary embodiment of a medicament dose carrier constructed in accordance with the present disclosure and having doses of medicament attached to a surface of the carrier, and wherein the carrier is shown being worked around a sharp corner to release doses of the medicament from the carrier as the carrier is bent around the corner; and FIG. 58 is a side elevation view of a further exemplary embodiment of a straw constructed in accordance with the present disclosure and including medicament dose containers, and wherein the straw is shown being worked around a sharp corner to successively open the dose containers as the containers are bent around the corner.

DETAILED DESCRIPTION OF EXEMPLARY EMBODIMENTS

Figure 1:
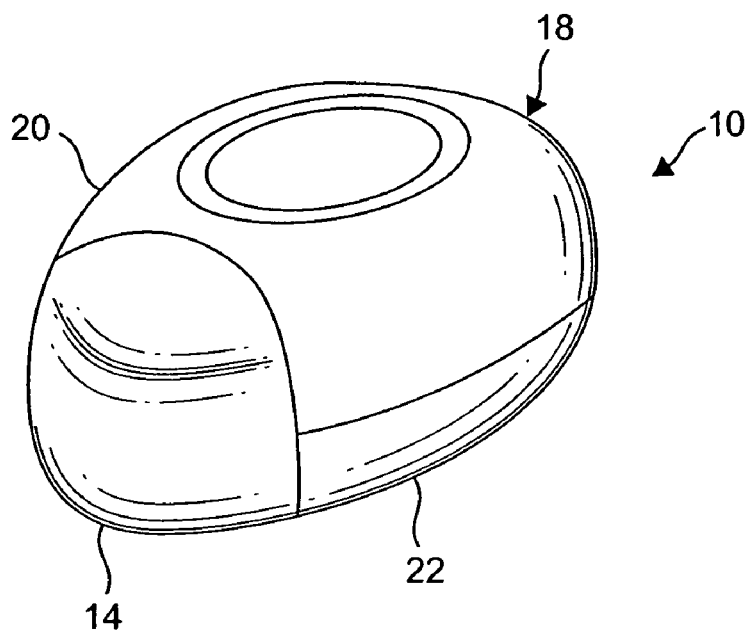
Figure 2:
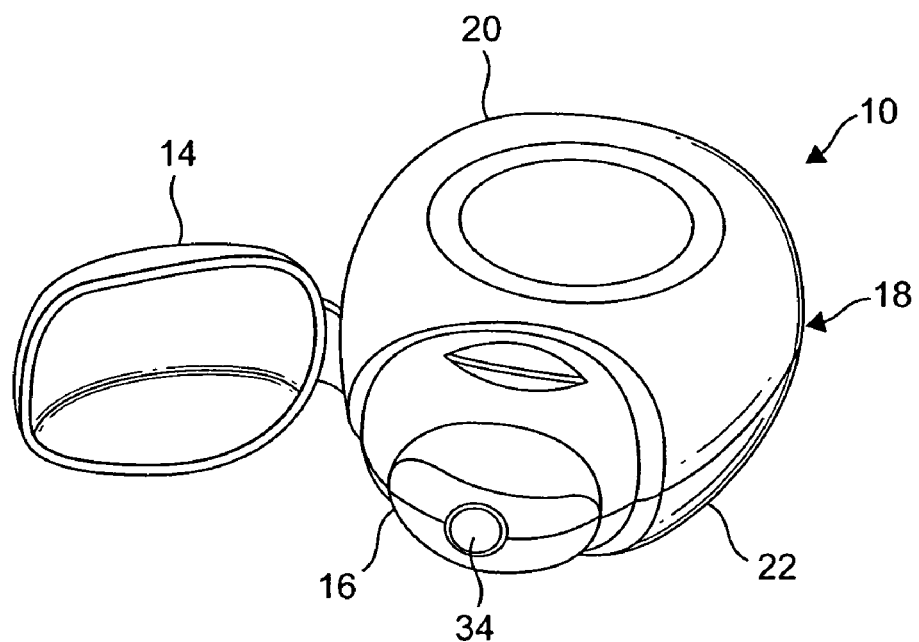

FIGS. 1 and 2 show an exemplary embodiment of a dry powder inhaler 10 constructed in accordance with the present disclosure. The dry powder inhaler 10 includes a pre-metered dose magazine 12 (not viewable in FIGS. 1 and 2 but shown in FIGS. 5 and 6) that consistently furnishes precise doses of dry powder, e.g., a dry powder medicament or medicament composition, for inhalation by a patient using the dry powder inhaler 10.

Figure 5:
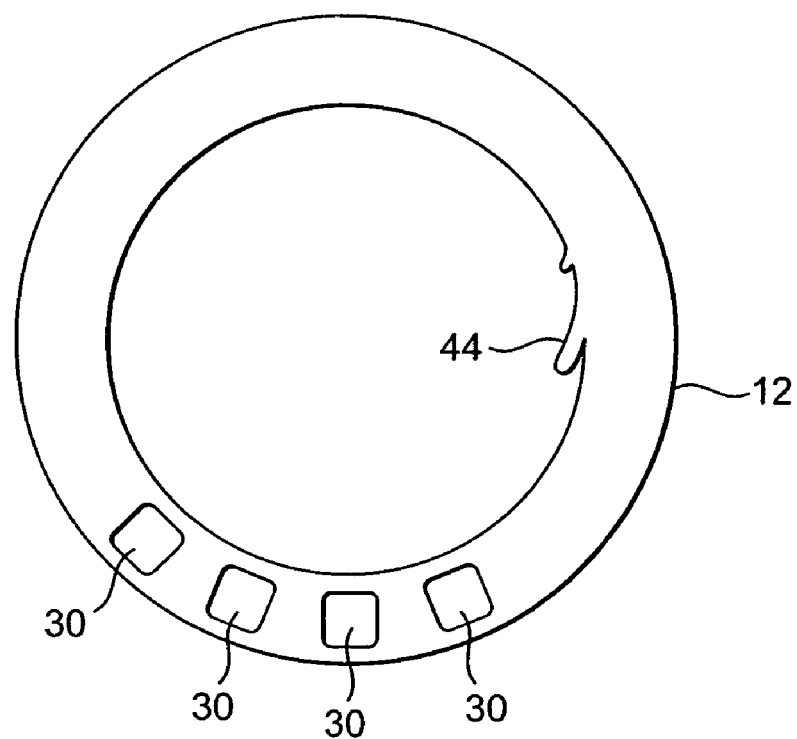
Figure 6:
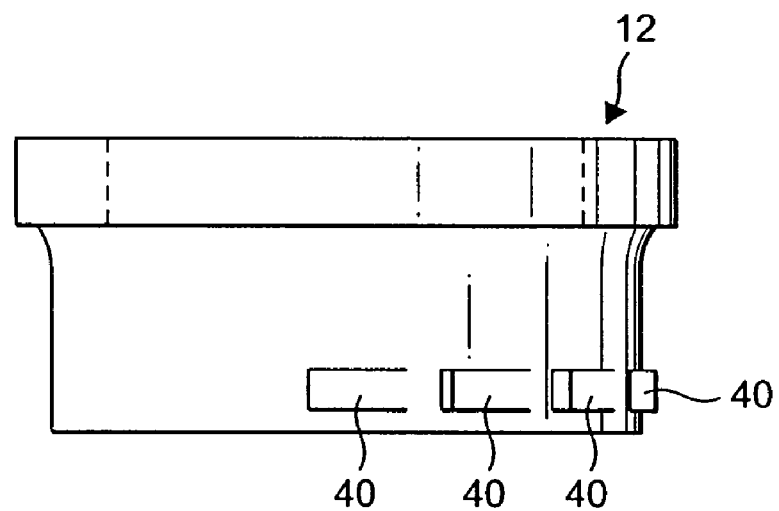
Figure 10:
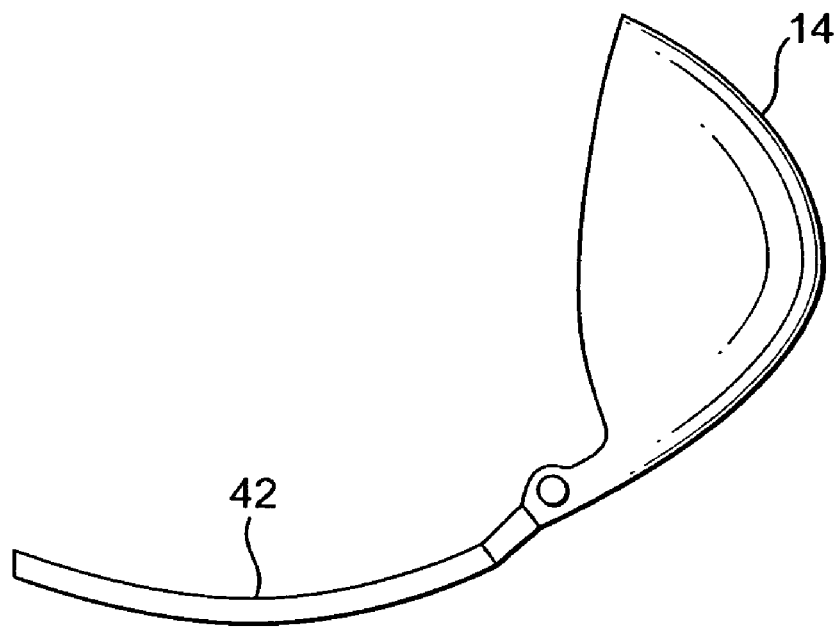
Figure 11:
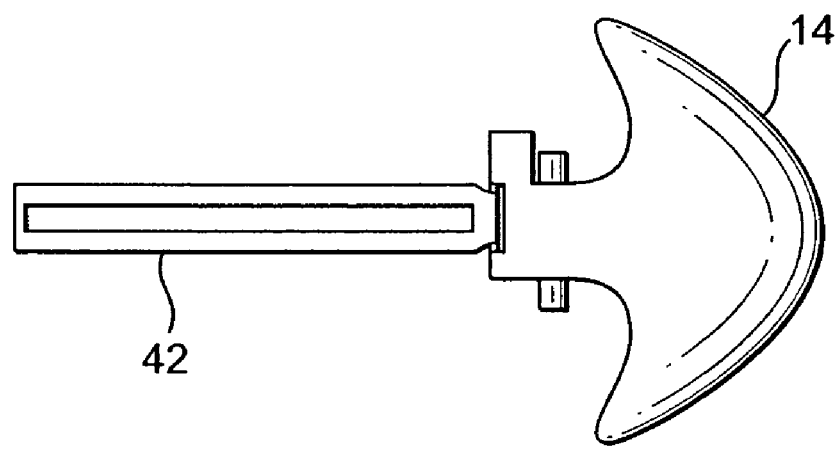

During use, the patient opens a mouthpiece cover 14 of the inhaler 10, inhales, then closes the cover. The mouthpiece cover 14 is also shown in FIGS. 10 and 11. The action of opening the cover 14 advances the pre-metered dose magazine 12, shown in FIGS. 5 and 6, presenting a dose for inhalation. If the cover 14 is closed without taking the dose, that dose is contained within the inhaler 10, and is not presented again for inhalation. Thus, there is no possibility for unintentional double dosing. Partial opening of the cover 14 will allow the user to see an indication of the number of doses remaining without advancing the magazine. Due to the individually sealed doses within the inhaler 10, a level of moisture protection is present with this inhaler.

Figure 3:
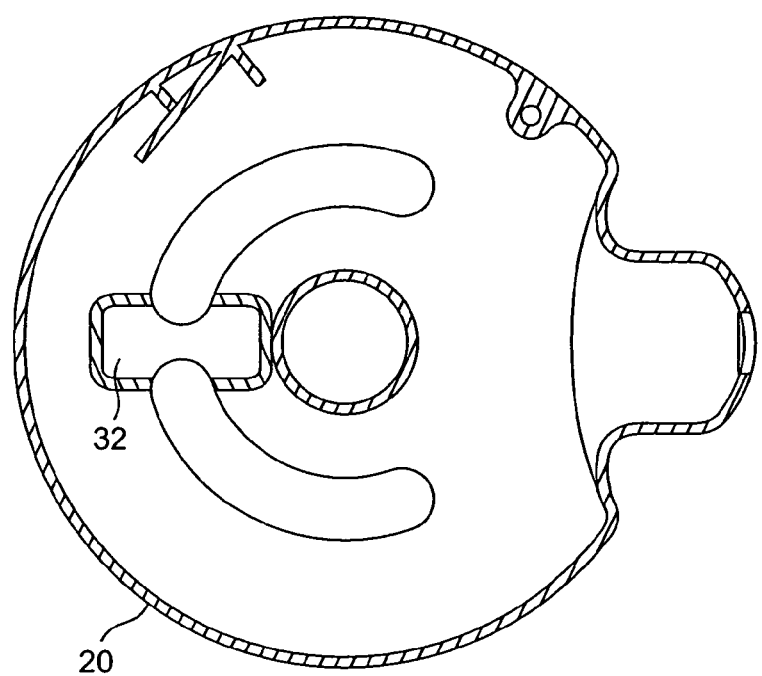
Figure 4:
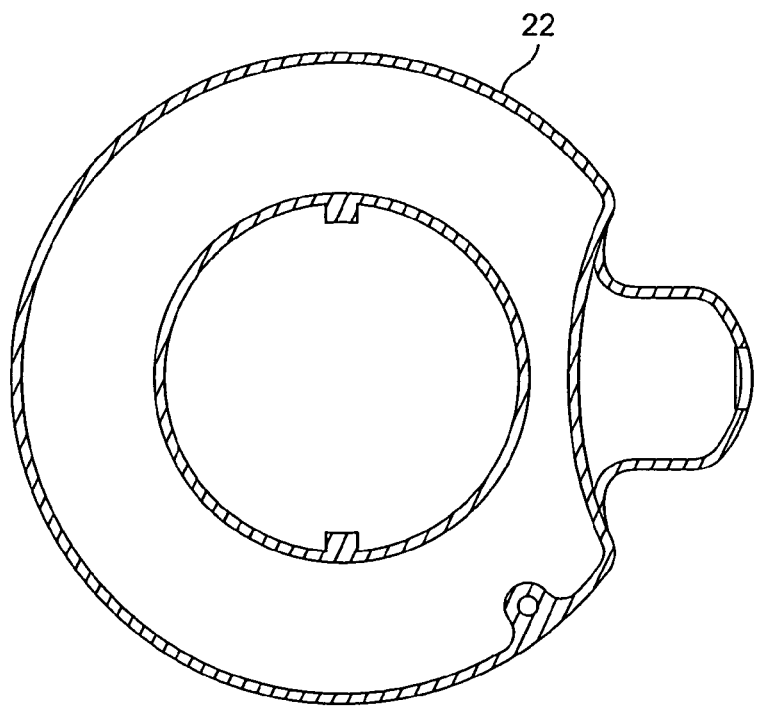

As shown in FIGS. 1 and 2, the inhaler 10 includes a housing 18 having an upper portion 20 mated to a lower portion 22. FIG. 3 is a bottom plan view of the upper portion 20 of the housing 18, and FIG. 4 is a top plan view of the lower portion 22 of the housing. FIGS. 5 and 6 show the dose magazine 12 of the inhaler 10 of FIGS. 1 and 2, and FIGS. 7 and 9 show a cup-like base 24 of a de-agglomerator of the inhaler 10 of FIGS. 1 and 2 and FIG. 8 shows a top piece 26 of the de-agglomerator. The cup-like base 24 is received in the lower portion 22 of the housing 18 and the dose magazine 12 is received for rotation over the top piece 26 of the de-agglomerator and guided by the upper portion 20 of the housing 18.

During operation, the magazine 12 is movable with respect to the upper portion 20 of the housing 18 for sequentially positioning reservoirs 30 of the magazine 12 within a delivery passageway 32 of the upper portion. Then, a breath-induced low pressure at an outlet port 34 (shown in FIGS. 7 and 9) of the de-agglomerator causes an air flow, through the dry powder delivery passageway 32 into a dry powder supply port 36 (shown in FIG. 8) of the de-agglomerator. As shown best in FIG. 3, the passageway 32 of the upper portion 20 includes a venturi (or venturi-type restriction) that causes the velocity of the breath-induced air flow to increase. The air pressure in the venturi decreases as a result of the increased velocity, and the drop in pressure causes the pre-metered dose of dry powder to be dragged from the reservoir 30 aligned with the passageway 32, and entrained into the air flow traveling to the de-agglomerator.

Preferably, the magazine 12 is movable with respect to the upper portion 20 of the housing for sequentially positioning the dry powder reservoirs 30 of the magazine within the delivery passageway 32 of the upper portion. However, it should be understood that the magazine 12 could be made stationary, and the upper portion 20 made moveable with respect to the magazine for sequentially positioning the passageway over the reservoirs.

The magazine 12 is provided with an annular shape such that rotation annular magazine sequentially positions the plurality of the dry powder reservoirs 30 within the delivery passageway 32 of the upper portion 20 of the housing 18. The annular magazine 12 includes teeth 40 extending radially outwardly that are engaged by a pivotal rake 42 of the mouthpiece cover 14 for advancing the magazine 12 upon the cover 14 being opened. FIGS. 10 and 11 show the magazine advancement rake 42 pivotally extending from the cover 14. The engagement rake 42 engages the teeth 40 of the magazine 12 to rotate and advance the magazine 12 upon the mouthpiece cover 14 being opened.

The dry powder reservoirs 30 are provided in the top surface of the magazine 12 and are uniformly sized and spaced with respect to one another. The magazine 12 preferably includes a seal over the top surface for sealing the doses of dry powder in the reservoirs 30 of the magazine in a moisture resistant and airtight manner prior to the reservoirs being positioned within the delivery passageway 32 of the upper portion 20. The seal can comprise, for example, a metal foil secured to the annular top surface of the magazine 12 with adhesive and covering the dry powder in the reservoirs 30 in a moisture resistant and airtight manner. The upper portion 20 of the housing 18 can include means for piercing the foil above each of the reservoirs 30 prior to the reservoirs being positioned within the delivery passageway 32 of the upper portion. The means for piercing can comprise, for example, a blade extending downward from the upper portion 20 of the housing 18 in front of the venturi of the delivery passageway 32.

It is intended that a manufacturer will fill the reservoirs 30 of the magazine 12 with properly metered individual doses of dry powder medicament, or medicament composition including medicament and a suitable particulate carrier such as lactose. The filled reservoirs 30 are then sealed in a moisture resistant and airtight manner, with the foil for example, and the magazine 12 and the upper portion 20 of the housing 18 are provided assembled as part of the inhaler 10. The inhaler 10 and the magazine 12 may be disposable. Alternatively, the dose magazine 12 may be removably insertable into a non-disposable inhaler 10 so that an empty magazine can be replaced by a full magazine.

Preferably, the magazine 12 is movable with respect to the upper portion 20 of the housing 18 through a plurality of discrete increments, wherein at each increment one of the plurality of the dry powder reservoirs 30 of the magazine is positioned within the delivery passageway 32 of the upper portion. In addition, the magazine 12 is preferably movable in a single direction only with respect to the housing 18, so that a user can access the reservoirs 30 in sequence, without being able to access one of the reservoirs 30 more than once. Furthermore, movement between the magazine 12 and the upper portion 20 of the housing is preferably prevented after all the dry powder reservoirs 30 of the magazine have been positioned in the delivery passageway 32 of the upper portion, to provide an indication to a patient that all of the doses of the magazine have been used. For example, the magazine 12 is provided with a radially inwardly extending catch 44, as shown in FIG. 5, that prevents further rotation of the magazine upon all of the reservoirs 30 passing through the delivery passageway 32 of the housing 18.

The inhaler 10 can also include an indicator for indicating the number of dry powder reservoirs 30 containing dry powder, i.e., the number of pre-metered doses remaining in the magazine 12. The indicator can comprise, for example, sequential printed numbers corresponding to the reservoirs 30 of the magazine 12 provided on the outer surface of the magazine, so that the number of reservoirs that have passed through the delivery passageway 32 of the upper portion 20 of the housing 18 can be determined by partly opening the cover 14 (without causing the magazine to advance) and viewing the numbers on the magazine. Although not shown, the inhaler can also be provided with a lock for locking the mouthpiece cover 14 in an opened or a closed position upon the advancement of a final medicament reservoir of the magazine.

As its name implies, the de-agglomerator breaks down agglomerates of dry powder before inhalation of the dry powder by a patient. The de-agglomerator includes two diametrically opposed inlet ports 46, that extend in a direction substantially tangential to the circular cross-section of the swirl chamber formed within the de-agglomerator. As a result, air flows entering the chamber through the inlet ports 46, are at least initially directed transverse with respect to the chamber and collide with the air flow entering through the supply port to create a combined turbulence air flow.

The de-agglomerator includes vanes 48 at the first end of the swirl chamber 52. The vanes 48 are sized such that at least a portion of the combined air flows collide with oblique surfaces of the vanes. The geometry of the swirl chamber 52 causes the combined air flows and the entrained dry powder to follow a turbulent spiral path, or vortex, through the chamber. Thus, particles and any agglomerates of the dry powder constantly impact against the wall of the swirl chamber and collide with each other, resulting in a mutual grinding or shattering action between the particles and agglomerates. In addition, particles and agglomerates deflected off the oblique surfaces of the vanes 48 cause further impacts and collisions. The constant impacts and collisions cause any agglomerates of dry powder to break into additional particles, and cause the particles to be substantially micronized.

Upon exiting the swirl chamber 52, the direction of the combined air flow and the entrained dry powder is again changed through the outlet port 34, which extends through the mouthpiece 16 of the housing 18. The combined air flow and the entrained dry powder retain a swirl component of the flow, such that the air flow and the entrained dry powder spirally swirls through the outlet port 34. Since the micronized powder and any remaining agglomerates maintain the swirl imparted from swirl chamber, the swirling flow causes additional impacts in the outlet port 34 so as to result in further breaking up of any remaining agglomerates prior to being inhaled by a patient. The de-agglomerator, therefore, ensures that particles of the dry powder are small enough for adequate penetration of the powder into a bronchial region of a patient's lungs during inhalation.

Figure 7:
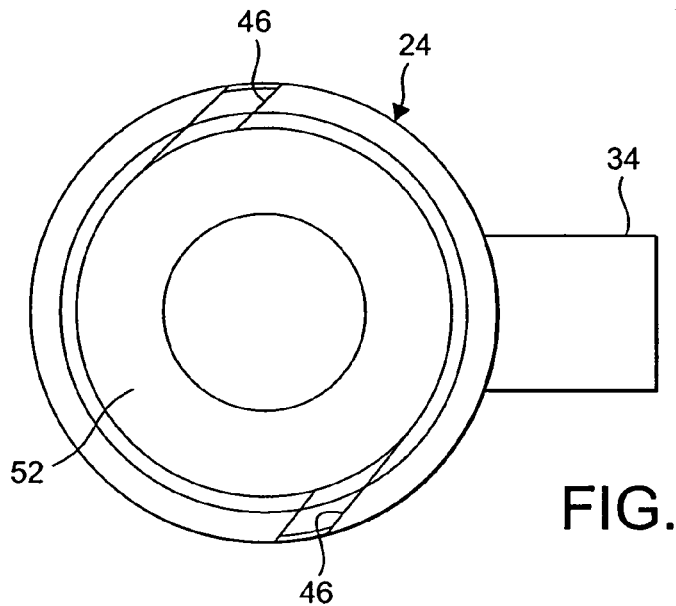
Figure 8:
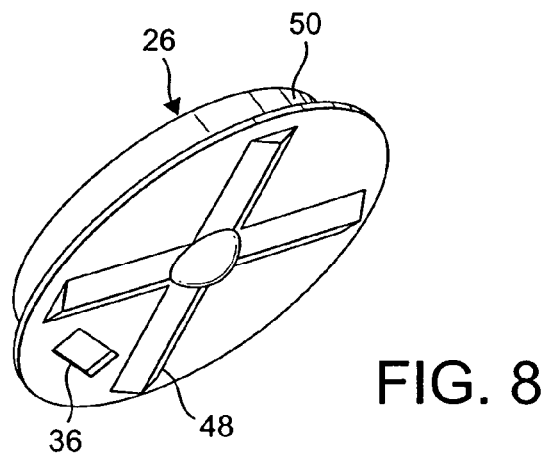
Figure 9:
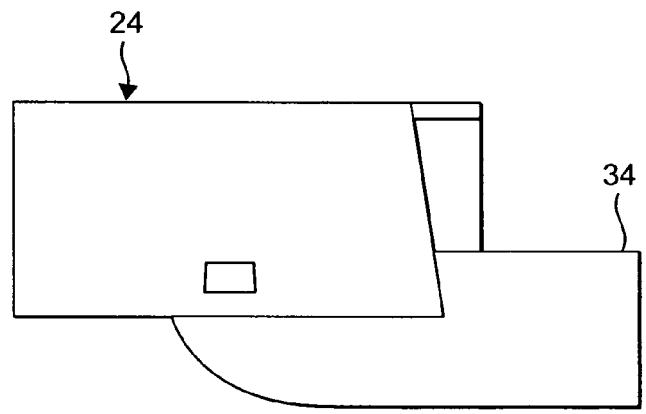

The de-agglomerator is assembled from two pieces: the cup-like base 24 shown in FIGS. 7 and 9, and the top piece 26 shown in FIG. 8, which are connected together to form the swirl chamber 52 within the de-agglomerator. The cup-like base 24 is secured in the lower portion 22 of the housing 18 and defines the outlet port 34 and the inlet ports 46. The top piece 26 forms the vanes 48 and defines the supply port 36.

The top piece 26 also includes an upwardly extending cylindrical guide 50, and a chimney (not viewable) extending upwardly from the supply port 36 within the guide, as shown best in FIG. 8. The inner circumference of the annular magazine 12 is received coaxially on the guide 50, such that the magazine can be rotated about the guide. A hood of the upper portion 20 of the housing 18 is received over the chimney of the supply port 36 to connect the delivery passageway 32 of the upper portion 30 with the supply port 36 of the de-agglomerator.

The de-agglomerator, the magazine and the housing are preferably manufactured from a plastic such as polypropylene, acetal or moulded polystyrene, but may be manufactured from metal or another suitable material.

The inhaler of FIGS. 1 through 11 may be used for any drug formulation which may be advantageously administered to the lung or nasal passages in an animal, to cure or alleviate any illness or its symptoms. Many medicaments, bioactive active substances and pharmaceutical compositions may be included in the dosage forms of the present invention. Non-limiting examples of classes of drugs contemplated for use include ace-inhibitors, acne drugs, alkaloids, amino acid preparations, anabolic preparations, analgesics, anesthetics, antacids, antianginal drugs, anti-anxiety agents, anti-arrhythmias, anti-asthmatics, antibiotics, anti-cholesterolemics, anti-coagulants, anti-convulsants, anti-depressants, anti-diabetic agents, anti-diarrhea preparations, antidotes, anti-emetics, anti-histamines, anti-hypertensive drugs, anti-inflammatory agents, anti-lipid agents, anti-manics, anti-nauseants, anti-nauseants, anti-neoplastics, anti-obesity drugs, anti-parkinsonism agents, anti-psychotics, anti-pyretics, anti-rheumatic agents, anti-spasmodics, anti-stroke agents, anti-thrombotic drugs, anti-thyroid preparations, anti-tumor drugs, anti-tussives, anti-ulcer agents, anti-uricemic drugs, anti-viral drugs, appetite stimulants or suppressants, biological response modifiers, blood modifiers, bone metabolism regulators, cardiovascular agents, central nervous system stimulates, cerebral dilators, cholinesterase inhibitors, contraceptives, coronary dilators, cough suppressants, decongestants, dietary supplements, diuretics, DNA and genetic modifying drugs, dopamine receptor agonists, endometriosis management agents, enzymes, erectile dysfunction therapies, erythropoietic drugs, expectorants, fertility agents, gastrointestinal agents, homeopathic remedies, hormones, hyper- and hypo-glycemic agents, hypercalcemia and hypocalcemia management agents, hypnotics, immunomodulators, immunosuppressives, ion exchange resins, laxatives, migraine preparations, motion sickness treatments, mucolytics, muscle relaxants, neuromuscular drugs, obesity management agents, osteoporosis preparations, oxytocics, parasympatholytics, parasympathomimetics, peripheral vasodilators, prostaglandins, psychotherapeutic agents, psycho-tropics, stimulants, respiratory agents, sedatives, smoking cessation aids, sympatholytics, systemic and non-systemic anti-infective agents, terine relaxants, thyroid and anti-thyroid preparations, tranquilizers, tremor preparations, urinary tract agents, vasoconstrictors, vasodilators, and combinations thereof.

In some embodiments of the invention, the dosage form for use with the invention comprises anti-inflammatory agents suitable for inhalation administration. Such anti-inflammatory agent may include, for example, bronchodilators and steroids. Representative $\beta_2$-adrenergic receptor agonist bronchodilators include, without limitation, salmeterol, formoterol, bambuterol, albuterol, terbutaline, pirbuterol, bitolterol, metaproterenol, isoetharine, isoproterenol, fenoterol, or procaterol. Non-limiting anti-inflammatory steroids contemplated for use with the invention include budesonide, beclomethasone, fluticasone, and triamcinolone diacetate. Additional anti-inflammatory agents contemplated include ipatropium bromide and sodium cromoglycate.

Therapeutically effective formulations and dosages to be administered using the devices described herein are well known to practitioners. One of skill in the art will appreciate that practitioners may opt to alter dosages and/or formulations to fit a particular patient/animal needs.

Figure 12:
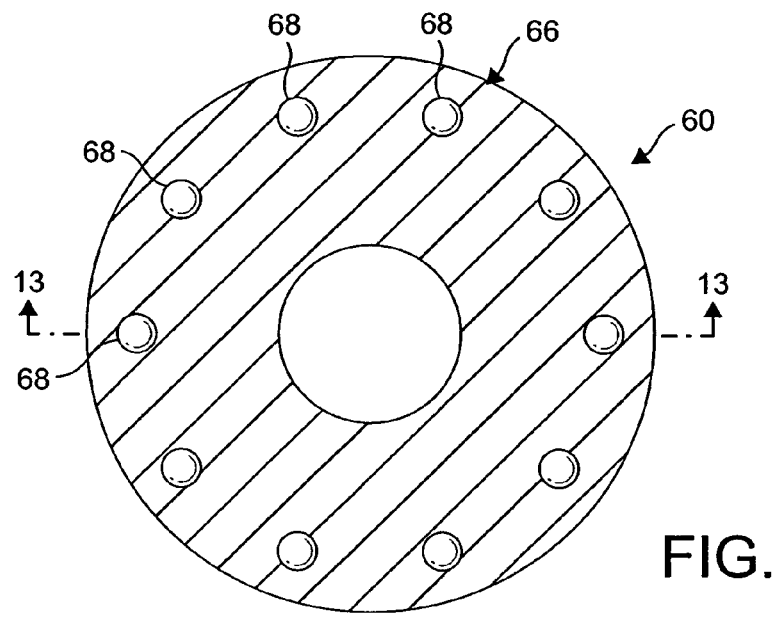
Figure 13:
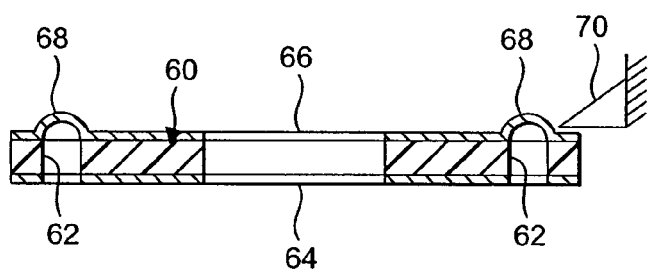
Figure 14:
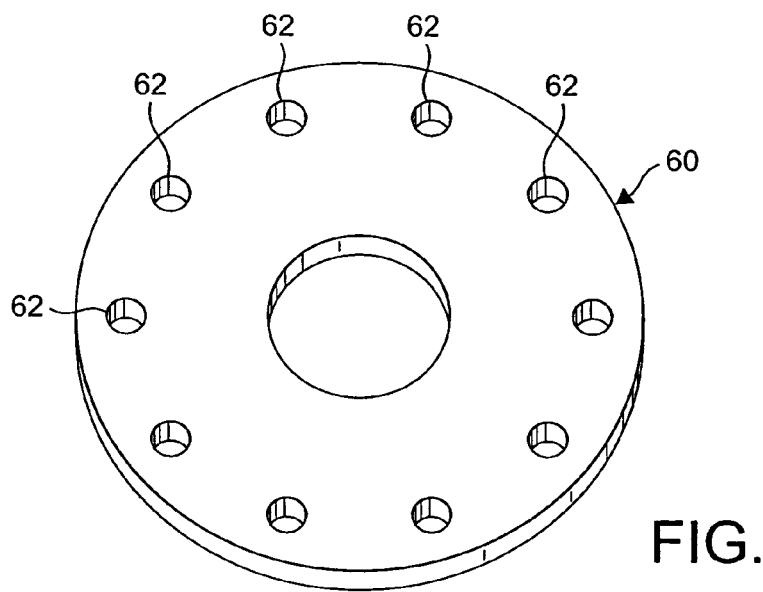

FIGS. 12 through 14 show an exemplary embodiment of a dose magazine 60 constructed in accordance with the present disclosure. The dose magazine 60 can be used for example with the inhaler of FIGS. 1 through 11. As shown in FIG. 14, the dose magazine 60 includes medicament reservoirs in the form of axial bores 62 for receiving medicament. As shown in FIGS. 12 and 13, the dose magazine 60 also includes a lower layer 64 of moisture resistant, air-tight material covering a lower surface of the magazine and an upper layer 66 of moisture resistant, air-tight material covering an upper surface of the magazine and enclosing medicament in the bores 62 of the magazine in a dry, air-tight manner. As shown best in FIG. 13, the upper layer 66 of moisture resistant, air-tight material can be provided with domes 68 over the medicament bores 62 so that a blade 70 can be positioned to successively cut open the domes 68 and release the medicament upon rotation of the magazine 60.

The moisture resistant, air-tight material can comprise, for example, metal foil secured to the magazine with adhesive. In addition, the foil layers may include selective adhesive, e.g., no adhesive positioned in contact with the medicament, in order to maintain dose uniformity. The moisture resistant, air-tight material can also comprise, for example, a laminate of metal foil secured a layer of plastic, which in turn is secured to the magazine with adhesive.

Figure 15:
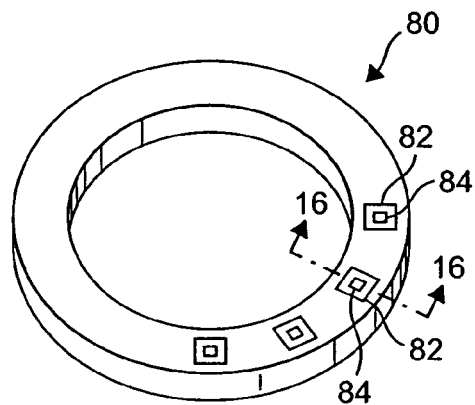
Figure 16:
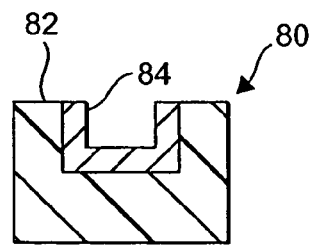

FIGS. 15 and 16 show another exemplary embodiment of a dose magazine 80 constructed in accordance with the present disclosure. As shown, the magazine 80 includes medicament reservoirs 82 and each medicament reservoir includes a lining 84 of moisture resistant, air-tight material, such as a metal insert or foil.

Figure 17:
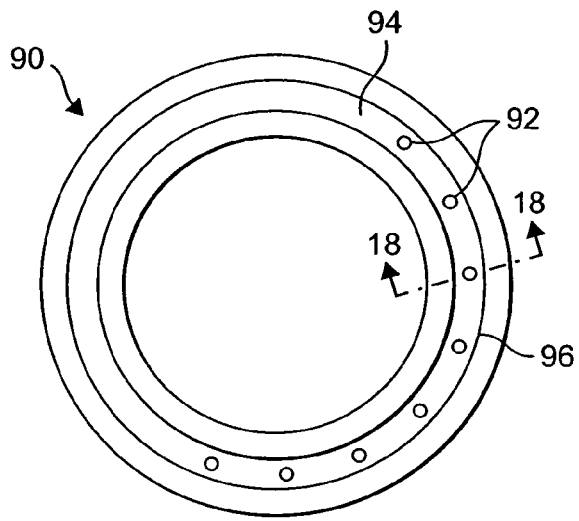
Figure 18:
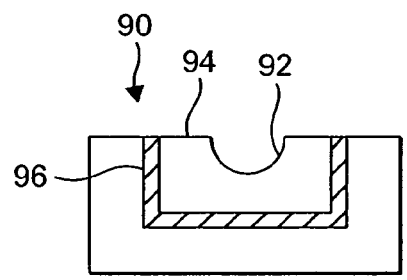
FIG. 18 is a sectional view of the dose magazine taken along line 18-18 of FIG. 17.

FIGS. 17 and 18 show an additional exemplary embodiment of a dose magazine 90 constructed in accordance with the present disclosure. As shown, the magazine 90 includes medicament reservoirs 92 formed in a trough 94 of a first material, such as plastic, which is formed in a trough 96 of moisture resistant, air-tight material, such as a metal. The metal trough 96 can be pre-formed via stamping or metal injection molding. The metal trough 96 can also be formed from a metal foil.

Figure 19:
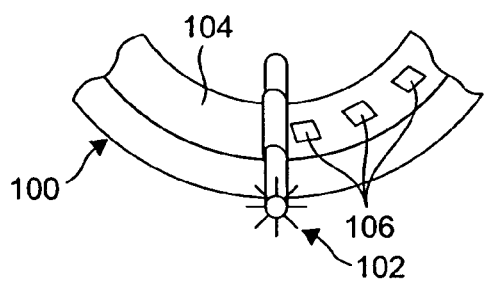
FIG. 19 is a top perspective view of a portion of a further exemplary embodiment of a dose magazine constructed in accordance with the present disclosure, and including a foil removal mechanism.

FIG. 19 shows a further exemplary embodiment of a dose magazine 100 constructed in accordance with the present disclosure, and including a foil removal mechanism 102. The foil removal mechanism comprises a rotatable winding wheel 102 which peels an upper layer 104 of moisture resistant, air-tight material, such as metal foil, from an upper surface of the magazine 100 as the magazine is rotated. As the foil 104 is peeled from the magazine 100, medicament reservoirs 106 are uncovered to allow inhalation of the medicament therein. The foil removal mechanism 102 can also be adapted and used to index the magazine 100.

Figure 20:
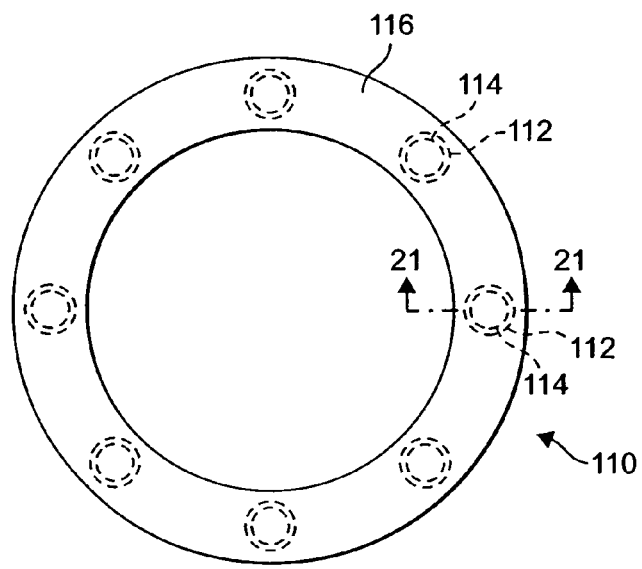
FIG. 20 is a top plan view of a further exemplary embodiment of a dose magazine constructed in accordance with the present disclosure.
Figure 21:
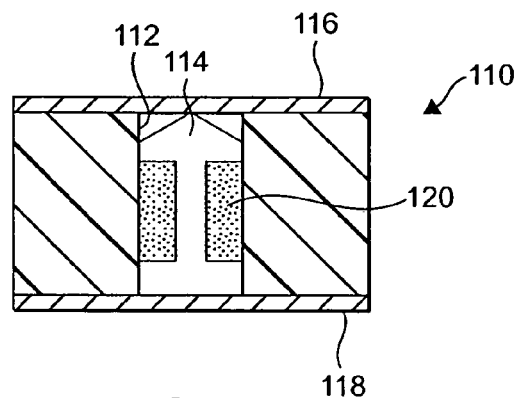
FIG. 21 is a sectional view of the dose magazine taken along line 21-21 of FIG. 20, showing a deployable medicament piston of the dose magazine.

FIGS. 20 and 21 show a further exemplary embodiment of a dose magazine 110 constructed in accordance with the present disclosure. The dose magazine 110 includes axial bores 112 containing deployable medicament pistons 114 sealed between layers 116, 118 of moisture resistant, air-tight material, such as metal foil. The pistons 114 each have at least one compartment 120 holding at least one dose of powder medicament, which are presented for inhalation upon the pistons 114 being pushed upwardly through the upper layer 116 of foil.

Figure 22:
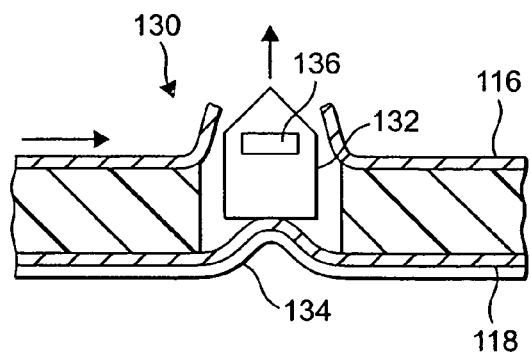
FIG. 22 is a sectional view of exemplary embodiments of a dose magazine, a medicament piston, and an actuator, which is shown deploying the piston, all constructed in accordance with the present disclosure.
Figure 23:
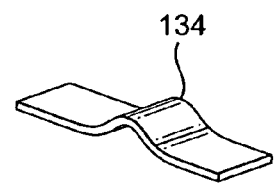
FIG. 23 is a perspective view of the actuator of FIG. 22.
Figure 31:
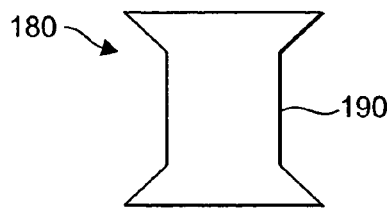
FIG. 31 is a side elevation view of another exemplary embodiment of a medicament piston constructed in accordance with the present disclosure.
Figure 32:
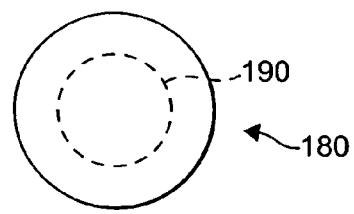
FIG. 32 is a top plan view of the medicament piston of FIG. 31.
Figure 33:
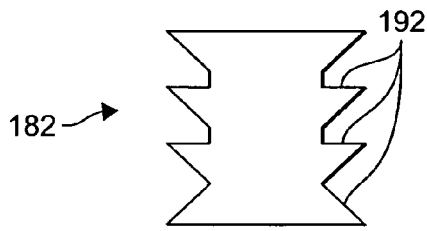
FIG. 33 is a side elevation view of an additional exemplary embodiment of a medicament piston constructed in accordance with the present disclosure.
Figure 34:
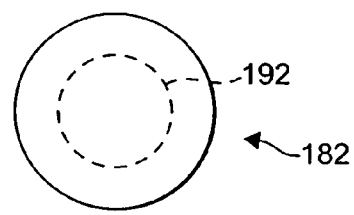
FIG. 34 is a top plan view of the medicament piston of FIG. 33.
Figure 35:
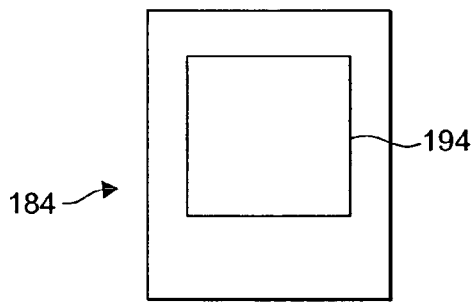
FIG. 35 is a side elevation view of another exemplary embodiment of a medicament piston constructed in accordance with the present disclosure.
Figure 36:
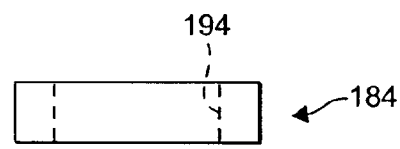
FIG. 36 is a top plan view of the medicament piston of FIG. 35.
Figure 37:
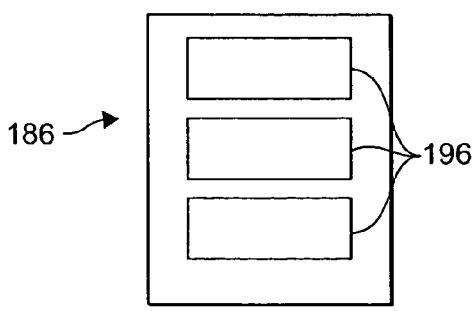
FIG. 37 is a side elevation view of an additional exemplary embodiment of a medicament piston constructed in accordance with the present disclosure.
Figure 38:
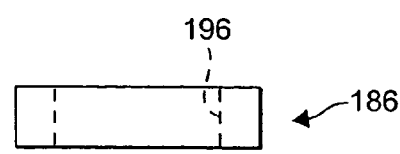
FIG. 38 is a top plan view of the medicament piston of FIG. 37.

FIG. 22 shows exemplary embodiments of a dose magazine 130, a medicament piston 132, and an actuator 134, which is shown deploying the piston, all constructed in accordance with the present disclosure. FIG. 23 is a perspective view of the actuator 134 of FIG. 22. As the magazine 130 is linearly moved over the actuator 134, the actuator 134 successively pushes the pistons 132 upwardly through the upper layer 116 of foil to expose a compartment 136 containing a dose of medicament for inhalation.

FIGS. 24 and 25 show additional exemplary embodiments of a dose magazine 140, a mouthpiece cover 142 and an actuator 144, all constructed in accordance with the present disclosure, and wherein the actuator 144 is adapted to cause a medicament piston 146 to be deployed from the magazine 140 upon the mouthpiece cover 142 being opened.

FIG. 26 shows a further exemplary embodiment of a dose magazine 150, a medicament piston 152, and an actuator 154 shown deploying the piston, all constructed in accordance with the present disclosure. The medicament piston 152 includes multiple, vertically arranged compartments in the form of shoulders 156a, 156b, 156c for holding dry powder medicament. By varying the amount that the piston 152 is extended through the upper layer 116 of foil, the amount of medicament for inhalation can be varied. For example, the piston 152 can be extended through the foil 116 so that only one 156a out of the three of the shoulders 156a, 156b, 156c of the piston extends above the foil so that a minimum dose is exposed for inhalation. Alternatively, the piston 152 can be extended through the foil 116 so that all of the shoulders 156a, 156b, 156c of the piston extend above the foil so that a maximum dose is exposed for inhalation.

FIGS. 27 through 30 show various exemplary embodiments of medicament pistons 160, 162, 164, 166 constructed in accordance with the present disclosure. The piston 160 of FIG. 27 includes vertically arranged shoulders 168a, 168b, 168c for supporting dry powder medicament, and the shoulders 168a, 168b, 168c become smaller towards the bottom of the piston 160. The piston 162 of FIG. 28 includes vertically arranged compartments 170a, 170b, 170c for holding dry powder medicament, and the compartments 170a, 170b, 170c become larger towards the bottom of the piston. The piston 164 of FIG. 29 includes vertically arranged shoulders 172 for holding dry powder medicament, and the shoulders are equally sized. The piston 166 of FIG. 30 includes vertically arranged compartments 174 for holding dry powder medicament, and the compartments are equally sized.

FIGS. 31 through 38 show further exemplary embodiments of medicament pistons 180, 182, 184, 186 constructed in accordance with the present disclosure. The piston 180 of FIGS. 31 and 32 has a circular cross-section and includes a single compartment 190 for holding dry powder medicament. The piston 182 of FIGS. 33 and 34 has a circular cross-section and includes vertically arranged shoulders 192 for holding dry powder medicament, and the shoulders 912 are equally sized. The piston 184 of FIGS. 35 and 36 has a rectangular cross-section and includes a single compartment 194 for holding dry powder medicament. The piston 186 of FIGS. 37 and 38 has a rectangular cross-section and includes vertically arranged compartments 196 for holding dry powder medicament, and the compartments 196 are equally sized.

Figure 39:
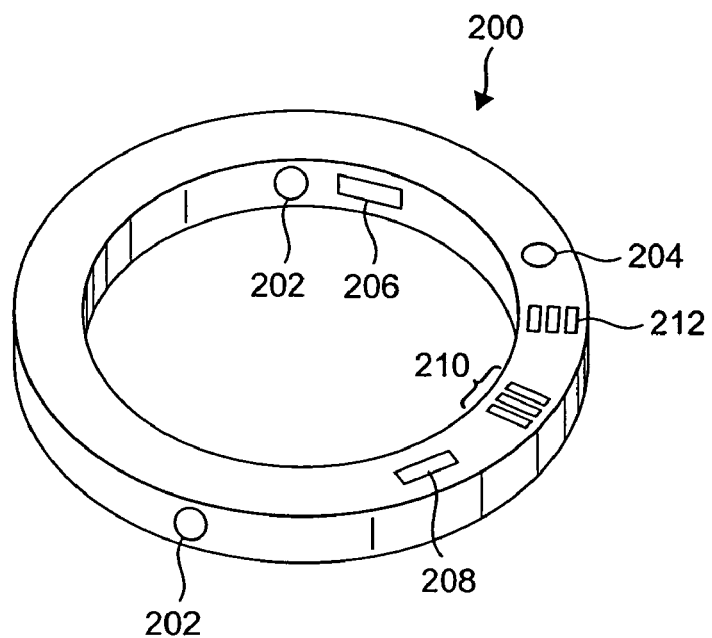
FIG. 39 is a top perspective view of a further exemplary embodiment of a dose magazine constructed in accordance with the present disclosure.

FIG. 39 is a top perspective view of a further exemplary embodiment of a dose magazine 200 constructed in accordance with the present disclosure. The dose magazine 200 includes examples of variously shaped and arranged bores for receiving deployable medicament pistons, such as the medicament pistons of FIGS. 27 through 38, for example. The magazine 200 can include, for example, circular bores 202 that extend radially through the magazine or circular bores 204 that extend axially through the magazine. The magazine 200 can also include rectangular bores 206 that extend radially through the magazine or rectangular bores 208 that extend axially through the magazine. In addition, the magazine 200 can include a set 210 of radially arranged, rectangular bores or a set 212 of radially extending, rectangular bores.

Figure 40:
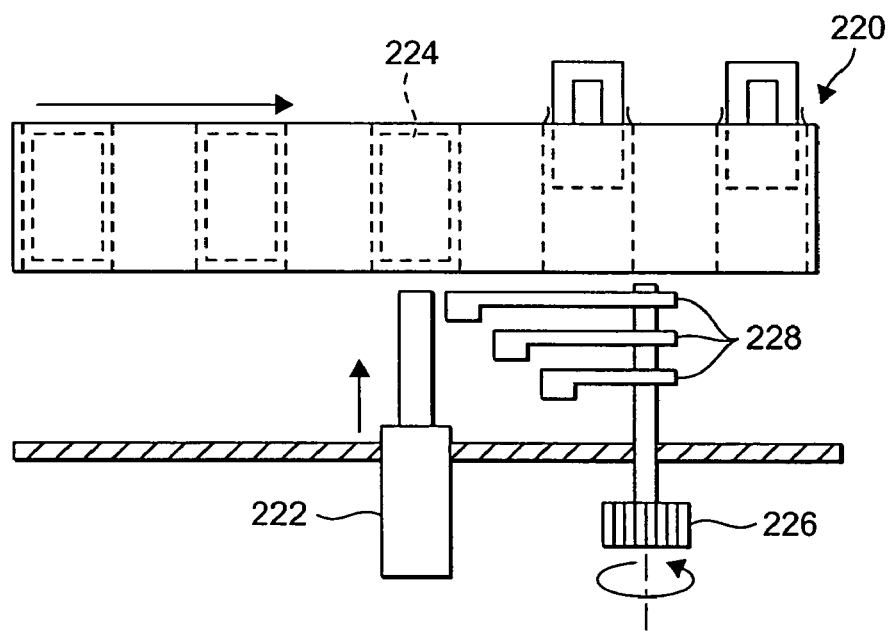
FIG. 40 is a side elevation view of exemplary embodiments of a dose magazine, an actuator for causing deployment of a medicament piston from the magazine, and an adjustment mechanism for adjusting the magnitude of deployment produced by the actuator, all constructed in accordance with the present disclosure.

FIG. 40 shows exemplary embodiments of a dose magazine 220, an actuator 222 for causing deployment of a medicament piston 224 from the magazine, and an adjustment mechanism 226 for adjusting the magnitude of deployment produced by the actuator, all constructed in accordance with the present disclosure. The adjustment mechanism 226 can be adjusted by a user to adjust the magnitude of deployment of the piston 224 produced by the actuator 222, so that the amount of dry powder medicament exposed for inhalation can be adjusted. The adjustment mechanism 226 includes shims 228 which prevent full motion of actuator 222, and a user can dial in the number of shims 228 corresponding to a desired dose.

Figure 41:
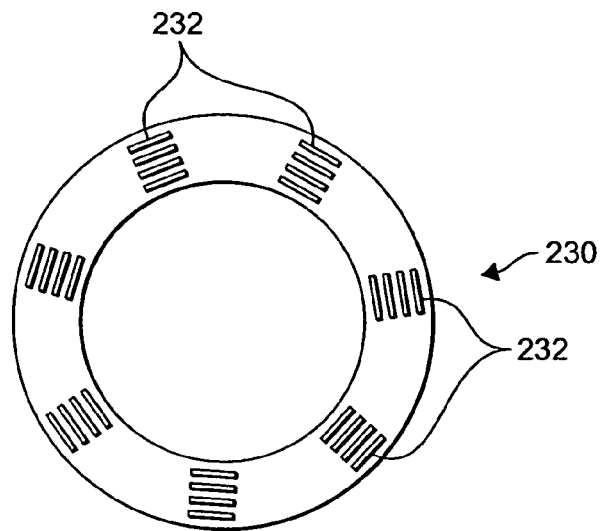
FIG. 41 is a top plan view of a further exemplary embodiment of a dose magazine constructed in accordance with the present disclosure and including sets of deployable medicament pistons.
Figure 42:
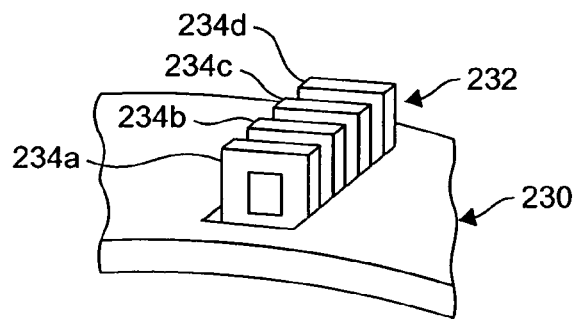
FIG. 42 is a side perspective view of a portion of the dose magazine of FIG. 41, wherein a set of the medicament pistons is shown deployed, or extended upwardly, from a top surface of the magazine.
Figure 43:
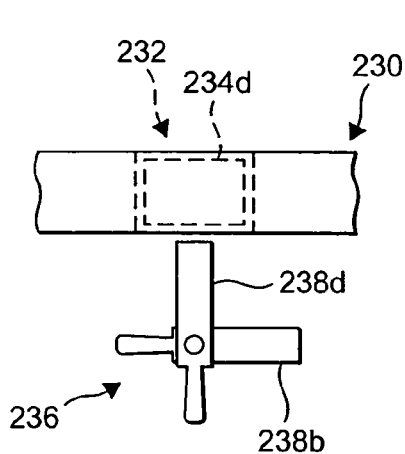
FIG. 43 is a side elevation view of a portion of the dose magazine of FIG. 41, showing a set of actuators for causing deployment of a set of the medicament pistons from the magazine, and wherein the actuators can be manipulated as desired to cause one or more of the pistons to be deployed.
Figure 44:
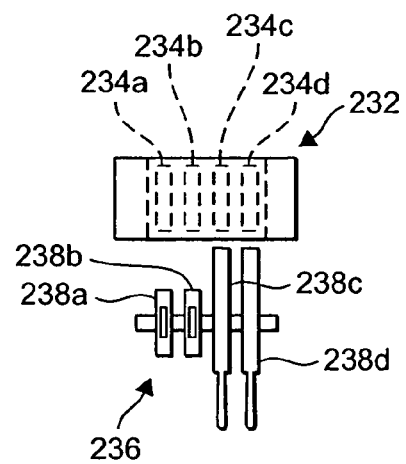
FIG. 44 is an end elevation view of a portion of the dose magazine of FIG. 41, showing the set of actuators, wherein two out of four of the actuators have been manipulated to cause deployment of pistons.

FIG. 41 is a top plan view of a further exemplary embodiment of a dose magazine 230 constructed in accordance with the present disclosure and including sets 232 of deployable medicament pistons, and FIG. 42 is a side perspective view of a portion of the dose magazine 230 of FIG. 41, wherein a set 232 of the medicament pistons 234a, 234b, 234c, 234d is shown deployed, or extended upwardly, from a top surface of the magazine. FIGS. 43 and 44 show a set 236 of actuators 238a, 238b, 238c, 238d for causing deployment of the set 232 of the medicament pistons 234a, 234b, 234c, 234d from the magazine. The actuators 238a, 238b, 238c, 238d can be manipulated as desired by a user to cause one or more of the pistons 234a, 234b, 234c, 234d to be deployed, so that the amount of dry powder medicament exposed for inhalation can be adjusted.

Figure 45:
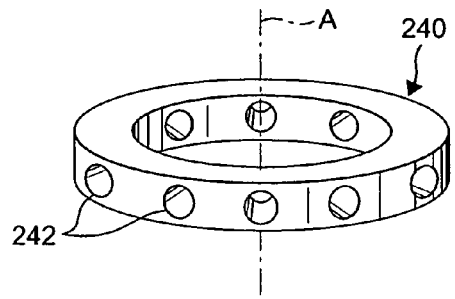
FIG. 45 is a top and side perspective view of a further exemplary embodiment of a dose magazine constructed in accordance with the present disclosure and including bores for receiving deployable medicament pistons, and wherein the bores extend radially with respect to an axis of the magazine.
Figure 46:
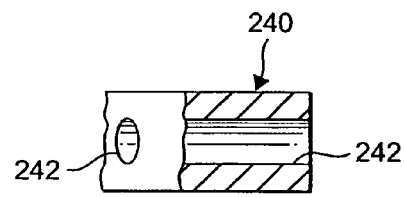
FIG. 46 is a sectional view of one of the bores of the dose magazine of FIG. 45.

FIGS. 45 and 46 show a further exemplary embodiment of a dose magazine 240 constructed in accordance with the present disclosure and including bores 242 for receiving deployable medicament pistons. The bores 242 extend radially with respect to an axis A of the magazine 240.

Figure 47:
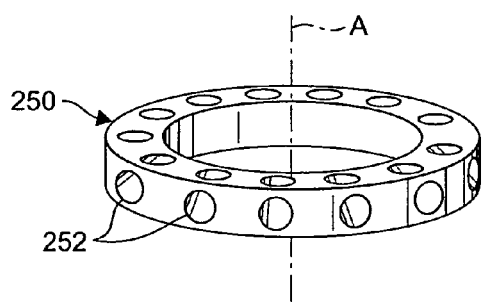
FIG. 47 is a top and side perspective view of another exemplary embodiment of a dose magazine constructed in accordance with the present disclosure and including bores for receiving deployable medicament pistons, wherein the bores extend radially and upwardly at an angle with respect to an axis of the magazine.
Figure 48:
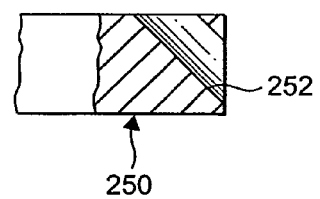
FIG. 48 is a sectional view of one of the bores of the dose magazine of FIG. 47.

FIGS. 47 and 48 show another exemplary embodiment of a dose magazine 250 constructed in accordance with the present disclosure and including bores 252 for receiving deployable medicament pistons. The bores 252 extend radially and at an angle with respect to an axis A of the magazine 250.

Figure 49:
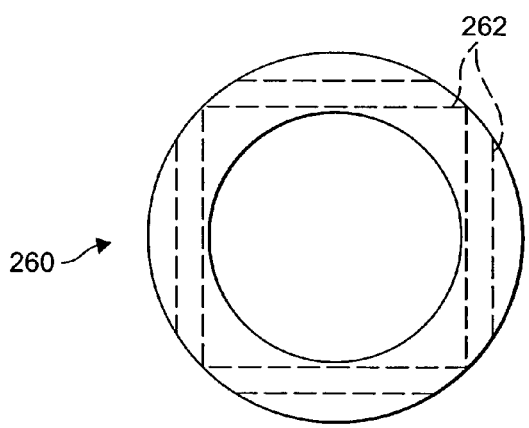
FIG. 49 is a top plan view of an additional exemplary embodiment of a dose magazine constructed in accordance with the present disclosure and including bores for receiving deployable medicament pistons, wherein the bores extend tangentially with respect to the magazine.

FIG. 49 show an additional exemplary embodiment of a dose magazine 260 constructed in accordance with the present disclosure and including bores 262 for receiving deployable medicament pistons. The bores 262 extend tangentially with respect to the magazine 260.

Figure 50:
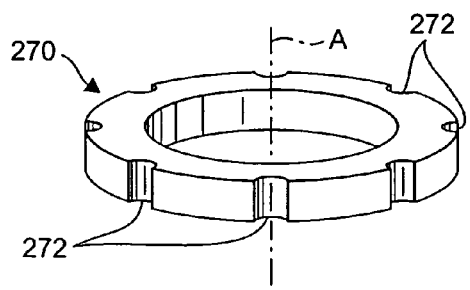
FIG. 50 is a top and side perspective view of another exemplary embodiment of a dose magazine constructed in accordance with the present disclosure and including bores for receiving deployable medicament pistons, wherein the bores are positioned at an outer circumference of the magazine and extend axially with respect to an axis of the magazine.

FIG. 50 show a further exemplary embodiment of a dose magazine 270 constructed in accordance with the present disclosure and including bores 272 for receiving deployable medicament pistons. The bores 272 are positioned at an outer circumference of the magazine 270 and extend axially with respect to an axis A of the magazine.

Figure 51:
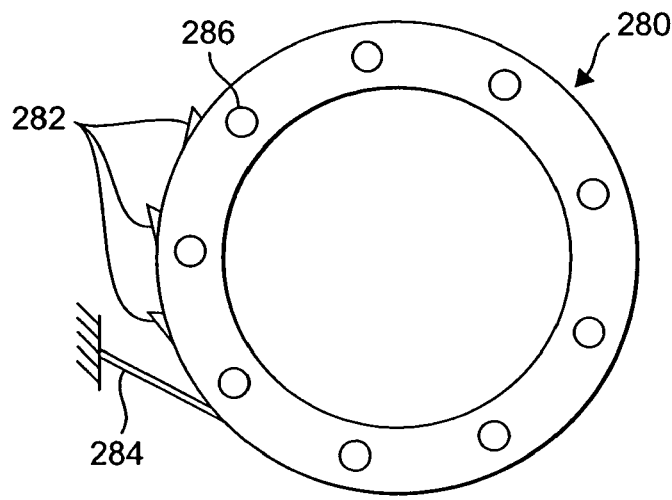
FIG. 51 is a top plan view of a further exemplary embodiment of a rotatable dose magazine constructed in accordance with the present disclosure and including radially extending teeth for engaging a pawl, as shown, to prevent reverse rotation of the magazine and to provide an indication of the advancement of a final dose of the magazine.

FIG. 51 shows a further exemplary embodiment of a rotatable dose magazine 280 constructed in accordance with the present disclosure and including radially extending teeth 282 for engaging a pawl 284, as shown, to prevent reverse rotation of the magazine 280 and to provide an indication of the advancement of a final medicament reservoir 286 of the magazine. This mechanism can be used to increase the force required to advance the magazine 280, increase noise or vibration, or provide other indication that the last medicament reservoir 286 is approaching and the inhaler should be refilled or replaced.

Figure 52:
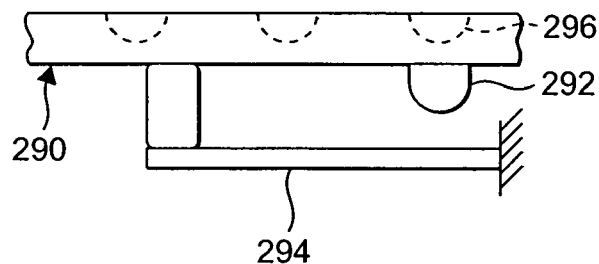
FIGS. 52 and 53 are side elevation views of an exemplary embodiment of a pawl constructed in accordance with the present disclosure, for engaging a dose magazine.
Figure 53:
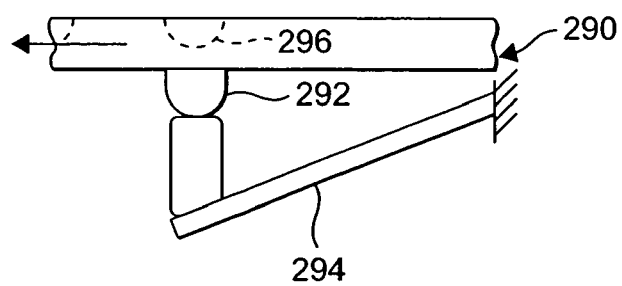

FIGS. 52 and 53 show an exemplary embodiment of a pawl 294 constructed in accordance with the present disclosure, for engaging a dose magazine 290. The pawl 294 can be adapted to provide a different sounding noise upon the advancement of a final medicament reservoir 296 and extending tooth 292 of the magazine 290.

Figure 54:
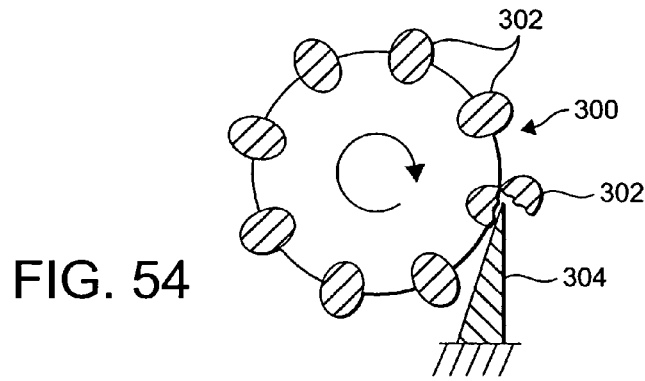
FIG. 54 is a top plan view of another exemplary embodiment of a rotatable dose magazine constructed in accordance with the present disclosure and including radially extending medicament dose containers, and wherein a fixed blade is positioned for successively opening the dose containers upon rotation of the magazine.

FIG. 54 shows another exemplary embodiment of a rotatable dose magazine 300 constructed in accordance with the present disclosure and including radially extending medicament dose containers 302 and a fixed blade 304 for successively opening the dose containers upon rotation of the magazine.

Figure 55:
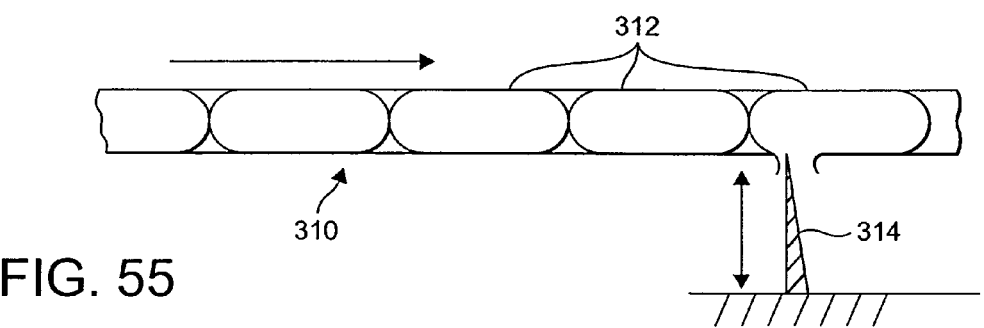
FIG. 55 is a side elevation view of an exemplary embodiment of a straw constructed in accordance with the present disclosure and including medicament dose containers, and wherein an exemplary embodiment of a blade constructed in accordance with the present disclosure for successively opening the dose containers upon linear movement of the straw is shown.

FIG. 55 shows an exemplary embodiment of a dose magazine 310 constructed in accordance with the present disclosure and including medicament dose containers 312, and wherein an exemplary embodiment of a blade 314 constructed in accordance with the present disclosure for successively opening the dose containers 312 upon linear movement of the magazine 310 is shown.

Figure 56:
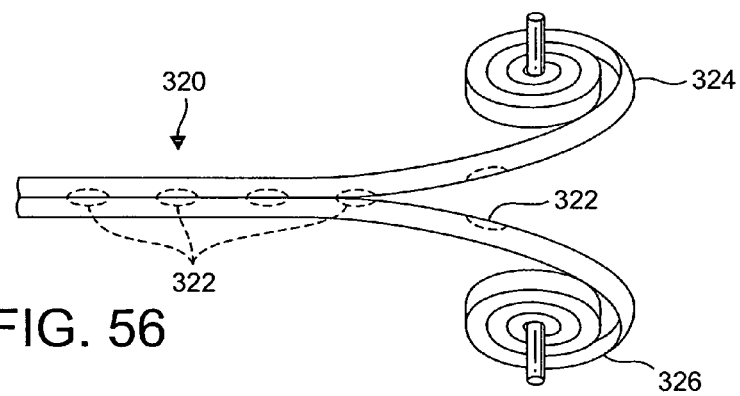
FIG. 56 is a side elevation view of another exemplary embodiment of a straw constructed in accordance with the present disclosure and including medicament dose containers, and wherein parallel layers of the straw are pealed apart and wound to cause linear movement of the straw and successively open the dose containers.

FIG. 56 shows another exemplary embodiment of a dose magazine 320 constructed in accordance with the present disclosure and including medicament dose containers 322, and wherein parallel layers 324, 326 of the dose magazine are peeled apart and wound to cause linear movement of the dose magazine 320 and successive opening of the dose containers 322 contained between the layers 324, 326.

FIG. 57 shows an exemplary embodiment of a medicament dose magazine 330 constructed in accordance with the present disclosure and having doses 332 of medicament attached to a surface of the magazine 330. The magazine 330 is made of elastic material and is drawn around a sharp corner 334 to successively release the doses 332 of the medicament from the magazine 330 as the magazine is bent around the corner 334.

FIG. 58 shows a further exemplary embodiment of a dose magazine 340 constructed in accordance with the present disclosure and including medicament dose containers 342. The dose magazine 340 is drawn around a sharp corner 344 to successively open the dose containers 342 as the containers are bent around the corner.

It should be understood that the foregoing detailed description and exemplary embodiments are only illustrative of a dry powder medicament inhaler and elements thereof according to the present disclosure. Various alternatives and modifications to the presently disclosed inhaler and inhaler elements can be devised by those skilled in the art without departing from the spirit and scope of the present disclosure. Accordingly, the present disclosure is intended to embrace all such alternatives and modifications that fall within the spirit and scope of the present disclosure and the following claims.

What is claimed is:

1. A dry powder inhaler, comprising:
   a housing having a mouthpiece and a delivery passageway connected to the mouthpiece;
   a magazine positioned within the housing and including a plurality of reservoirs for holding doses of dry powder, the magazine being movable within the housing to sequentially position the reservoirs within the delivery passageway;
   a cover connected to the housing and selectively movable to open and close access to the mouthpiece; and
   a rake connected to the cover and extending into the housing, the rake being engageable with the magazine so that, upon movement of the cover to open access to the mouthpiece, the rake moves the magazine and causes one of the reservoirs to be positioned within the delivery passageway;

wherein the magazine includes bores sealed with at least one layer of moisture resistant, air-tight material, and deployable pistons contained in the bores, and each of the pistons has at least one compartment holding powder medicament which is presented for inhalation upon the piston being pushed through the layer of moisture resistant, air-tight material.

2. An inhaler according to claim 1, further comprising an actuator for successively deploying the pistons from the magazine as the magazine is moved over the actuator.

3. An inhaler according to claim 1, further comprising an actuator connected to the cover for successively deploying the pistons from the magazine upon movement of the cover to open access to the mouthpiece.

4. An inhaler according to claim 1, wherein the medicament pistons each include multiple compartments.

5. An inhaler according to claim 4 wherein, for each of the medicament pistons, the multiple compartments vary in size.

6. An inhaler according to claim 4, further comprising an actuator for deploying the pistons from the magazine as the magazine is moved over the actuator, and an adjustment mechanism for adjusting the magnitude of deployment produced by the actuator.

7. An inhaler according to claim 1, wherein the bores are one of circular bores that extend radially through the magazine, circular bores that extend axially through the magazine, rectangular bores that extend radially through the magazine, and rectangular bores that extend axially through the magazine.

8. An inhaler according to claim 1, wherein the magazine includes sets of multiple bores each containing a deployable set of medicament pistons, the inhaler further comprising a set of deployable actuators for causing deployment of the set of the pistons from the magazine.

9. A dose magazine for a dry powder inhaler, comprising:

a plurality of reservoirs extending between a lower surface and an upper surface of the magazine, the magazine being movable within a housing of a dry powder inhaler so that the reservoirs are sequentially positioned within a delivery passageway of the housing of the dry powder inhaler upon movement of the magazine;

a lower layer of moisture resistant, air-tight material covering the ends of the reservoirs in the lower surface of the magazine;

an upper layer of moisture resistant, air-tight material covering the ends of the reservoirs in the upper surface of the magazine, such that the layers of moisture resistant, air-tight material enclose the reservoirs of the magazine in a substantially dry, air-tight manner; and deployable medicament pistons positioned in the reservoirs, each piston including at least one chamber for holding dry powder medicament, so that deployment of the piston through one of the layers of moisture resistant, air-tight material presents the dry powder medicament to the delivery passageway of the dry powder inhaler for inhalation, wherein the dose magazine includes sets of multiple bores each containing a deployable set of medicament pistons, and the inhaler includes a set of deployable actuators for causing deployment of the set of pistons from the magazine.

10. A dose magazine according to claim 9, wherein the medicament pistons each include multiple compartments.

11. A dose magazine according to claim 10, wherein, for each of the medicament pistons, the multiple compartments vary in size.

12. A dry powder inhaler, comprising:

a housing having a mouthpiece and a delivery passageway connected to the mouthpiece;

a dose magazine, including:

a plurality of reservoirs extending between a lower surface and an upper surface of the magazine, the magazine being movable within the housing so that the reservoirs are sequentially positioned within the delivery passageway of the housing upon movement of the magazine;

a lower layer of moisture resistant, air-tight material covering the ends of the reservoirs in the lower surface of the magazine;

an upper layer of moisture resistant, air-tight material covering the ends of the reservoirs in the upper surface of the magazine such that the layers of moisture resistant, air-tight material enclose the reservoirs of the magazine in a substantially dry, air-tight manner; and deployable medicament pistons positioned in the reservoirs, each piston including at least one chamber for holding dry powder medicament so that deployment of the piston through one of the layers of moisture resistant, air-tight material presents the dry powder medicament to the delivery passageway of the housing for inhalation; and an actuator for successively deploying the pistons from the magazine as the magazine is moved over the actuator.

13. An inhaler according to claim 12, further comprising an adjustment mechanism for adjusting the magnitude of deployment produced by the actuator.

* * * * *